United States Patent [19]
Salonen et al.

[11] Patent Number: 5,891,233
[45] Date of Patent: Apr. 6, 1999

[54] USE OF BIOACTIVE SILICIOUS GLASS AND NEW COMPOSITIONS CONTAINING BIOACTIVE SILICIOUS GLASS

[75] Inventors: Jukka Salonen, Turku; Ulla Tuominen, Ilmarinen; Antti Yli-Urpo, Littoinen, all of Finland

[73] Assignee: Bioxid Oy, Turku, Finland

[21] Appl. No.: 809,867

[22] PCT Filed: Oct. 2, 1995

[86] PCT No.: PCT/FI95/00539

§ 371 Date: Apr. 2, 1997

§ 102(e) Date: Apr. 2, 1997

[87] PCT Pub. No.: WO96/10985

PCT Pub. Date: Apr. 18, 1996

[30] Foreign Application Priority Data

Oct. 6, 1994 [FI] Finland ................................. 944672

[51] Int. Cl.[6] .................................................. C03C 3/078
[52] U.S. Cl. ..................... 106/35; 433/215.1; 433/78; 501/24; 501/25; 501/57; 501/58; 501/63; 501/72
[58] Field of Search ......................... 106/35; 433/215.1, 433/78; 501/24, 25, 57, 58, 63, 72

[56] References Cited

U.S. PATENT DOCUMENTS

| | | | |
|---|---|---|---|
| 3,981,736 | 9/1976 | Broemer et al. | 106/39.6 |
| 4,131,597 | 12/1978 | Bluethen et al. | 260/42.11 |
| 5,735,942 | 4/1998 | Litkowski et al. | 106/35 |

FOREIGN PATENT DOCUMENTS

| | | |
|---|---|---|
| 0415538 A3 | 6/1991 | European Pat. Off. . |
| 0511868 A2 | 11/1992 | European Pat. Off. . |
| 91/17777 A2 | 11/1991 | WIPO . |
| 93/20858 A1 | 10/1993 | WIPO . |
| 97/27148 | 7/1997 | WIPO . |

OTHER PUBLICATIONS

*Plastics That Don't Last*, New Scandinavian Technology, Nov. 4, 1992.

Primary Examiner—James H. Reamer
Attorney, Agent, or Firm—Adduci, Mastriani & Schaumberg, L.L.P.

[57] ABSTRACT

A pharmaceutical preparation, including a glass phase which is bioactive silica containing glass in the form of a paste, suspension or solution mixed in a physiologically suitable liquid or bound to a physiologically suitable vehicle, and which preparation reduces the pulpal irritation or a tooth and/or strengthens the structure of a tooth. Bioactive silica containing glass may be a material which contains only Si-oxide or Si-hydroxide and which allows the formation and movement of Si—OH-groups. Preferably, the preparation also contains calcium and phosphate sources.

20 Claims, 14 Drawing Sheets

A = BIOACTIVE AREA
B = INERT AREA
C = SOLUBLE GLASS
D = NO GLASS FORMATION

USE OF BIOACTIVE SILICIOUS GLASS AND NEW COMPOSITIONS CONTAINING BIOACTIVE SILICIOUS GLASS

This application is a 371 of PCT/FI95/00539, filed Oct. 2, 1995.

The aim of this invention is to introduce a novel use of bioactive glass and new preparations comprising bioactive silica containing glass. The said preparations can be used for reinforcing a tooth and for closing the dentinal tubules in the dentine in order to reduce pain transmitted to the pulp as a consequence of open tubules.

BACKGROUND OF THE INVENTION

Dentine forms the frame of a tooth. It surrounds the pulp and is covered by enamel on the crown and cementum on the root. The cementum does not always meet the edge of the enamel at the cementum-enamel junction. In such cases, dentine, which is not protected by another type of hard tissue, is exposed at the neck of a tooth. In the young, this area is usually covered by gingiva which covers this particular zone of dentine and prevents its exposure to irritation from the oral cavity.

Dentine consists of an extracellular matrix, which is formed by odontoblasts lining the pulp cavity. When dentine is formed and it becomes thicker, each odontoblast leaves behind a cell extension i.e. an odontoblast process. These processes remain inside the developing tissue and form dentinal tubules, which extend from the enamel-dentine/cementum-dentine border into the pulp. When exposed, open dentinal tubules form a link between the dentine surface and the pulp.

The structure of dentine is shown in detail in FIG. 1.

Once the tooth has stopped growing, odontoblasts continue their function and form secondary dentine on the pulp side of the tooth. They also form hard tissue i.e. intratubular dentine which gradually closes the tubules around the receding odontoblast processes (FIG. 2.). The level of mineralisation of intratubular dentine is significantly higher than that of intertubular dentine. The mineralisation of dentinal tubules is a very slow but natural process, associated with the ageing of a tooth. The slow pace and unpredictability of the process are manifested as problems in various clinical situations.

The hydrodynamic pain transmission mechanism of exposed dentine can be described as follows:

Dentinal tubules are 1–2 $\mu$m in diameter. When a section is cut perpendicular to the dentine surface, there are around 30 000–40 000 dentinal tubules per $mm^2$. A dentinal tubule is filled with an odontoblast process, surrounded by fluid from the pulp. A very strong capillary force prevails in open and exposed dentinal tubules. Consequently, fluid mechanically removed from the opening of the tubule is quickly replaced by fluid flowing out from the pulp. Similarly, substances with strong osmotic pressure (e.g. sweet solutions) cause an outward flow of fluids in the tubule, which in turn, leads to transformations of the odontoblasts lining the pulp chamber and tissues surrounding ondontoblasts, thus activating the nerve endings. On the other hand, irritation transmitted to the pulp may be caused by the inward flow of the fluid in the dentinal tubule. In practice, the hydrodynamic mechanism refers to the fluid flow in a dentinal tubule caused by a stimulus and the resulting hydraulic vibration in the pulp. According to current opinion and experience, the closing of the tubule and the resulting complete or partial prevention of fluid flow would lead to a reduction or even elimination of nerve activation, sensed as pain regardless of the primary stimulus (1). The pain transmission mechanism is illustrated in FIG. 3.

Clinical Problems

The exposure of dentine and dentinal tubules leading to the pulp may be the result of caries. The hard tissue (enamel/cementum) protecting the dentine is destroyed during the decay process. The situation leads to the known painful symptoms associated with cavity formation. The pain results from irritation which is transmitted to the pulp nerve endings through the dentinal tubules. During the decay process, partial mineralisation of tubule contents is usually observed. This is a consequence of the high calcium and phosphate ion concentration caused by demineralisation processes of the enamel and dentine in the close vicinity of intact dentine tissue. Strengthening of this phenomenon and its incorporation into the properties of filling materials would be desirable.

Exposure of dentine is also often associated with the periodontal diseases of a tooth, and also with the normal ageing process and dental hygiene habits. In certain cases, even in the young, the gingiva recesses or teeth erupt so that the necks of the teeth become exposed. This itself may lead to strong painful symptoms, in patients whose dentine was not covered by the protective and non-sensitive cementum in the first place. More often, however, exposure of dentine is associated with wrong toothbrushing habits, either using too heavy a hand, a coarse brush or the wrong technique. This results in worn and hypersensitive teeth, which affects the person's tolerance of hot/cold/bitter/sweet drinks and food, makes breathing more difficult in the hot and cold, and also interferes with proper oral hygiene.

Infections in the periodontal tissues and, especially, the treatment of periodontal infections, generally lead to gingival recession and exposure of dentine, often of fairly large areas. As successful therapy involves the removal of the root cementum protecting dentine, and polishing, which wears the teeth further, it is obvious that the general consequence of such treatment (25%) is the exposure of tooth necks and hypersensitivity. If the patient is fairly elderly and their dentinal tubules exhibit a substantial layer of highly mineralised intra-tubular dentine, the post-treatment pain is less severe. On the other hand, the pain resulting from the treatment may, in certain cases, be strong, it can continue for weeks and may require the use of analgetics. In the most extreme cases, irritation may lead to infection and, subsequently, to the death of a tooth and root canal treatment. In association with dental care, hypersensitive teeth is an irritating problem which occurs frequently, and should have a simple and inexpensive cure (2). FIG. 4 shows a tooth and the area with the exposed dentinal surface.

Known Methods of Treatment

Tooth ache, resulting from cavity formation refers, regardless of its similarities to hypersensitive dentine, to a different problem area. Sensitivity associated with caries, and pain caused by irritation is usually treated by fillings. At the bottom of the prepared cavity, a commercially available preparation is placed against the pulp, the biologically active component of such preparation is usually calcium hydroxide ($CaOH_2$). At the cell level, the strongly alkaline calciumhydroxide first induces irritation, which leads to the necrotisation of the tissue. Over a longer time span, however, it promotes the healing process. The result of the treatment is the formation of reparative secondary dentine. The formed tissue layer separates the pulp from the damaged area or the filling, but its effect on the mineralisation of dentine tubules is minimal.

During filling, the dentinal tubules can also be closed by glass ionomer cement, or with different preparations based on polymer chemistry (binder plastics, resins, dentine adhesives). These substances close dentinal tubules mechanically and improve the retention of the filling being prepared. Fluoride which is released from the glass ionomer cement may, in theory, have a positive effect on the mineralisation process of dentinal tubules. However, there are no research results of the possible clinical role of this phenomenon. Plastic-based preparations have no biological effects which promote the healing process and/or the formation of hard tissue between the pulp and the damaged and restored area.

The epidemiological data describing the extent of the problem caused by hypersensitive dentine and the need for its treatment is limited. In practice, dentine hypersensitivity is a common and typically highly variable problem. Because the symptoms are linked closely to the behaviour of a person and, in the long run, disappear; and because there are commercially available toothpastes, which may lower the sensitivity, the actual extent of the problem is difficult to define solely on the basis of how often people seek for professional help at their dentist's for this particular problem. In association with the treatment of inflamed gingivae and supportive tissues of the teeth, the need to offer relief for hypersensitive teeth is often acute.

Nowadays, two different concepts of treatment for hypersensitive teeth are available. These treatments are based on either raising the pain threshold of a tooth, or on the formation of a protective mineralisation precipitate either on the surface of a tooth or, preferably, in the dentinal tubules. In addition, the treatment involves gentle (possibly chemical) plaque control, diet guidance and confirmation that the irritation threshold of the pulp is not lowered by masticational overload or a poor filling which maintains chronic infection in the pulp.

For a long time, some toothpastes have contained substances designed to give relief to hypersensitive teeth (3, 4, 5, 6). The goal has been either the denaturation (formaldehyde) of the contents of the dentinal tubule or the formation of mineral precipitates (strontium chloride, fluorides, abrasives).

Sodiumfluorophosphate may infact have some therapeutic effects. Potassiumnitrate and potassiumcitrate reduce the irritability of the pulpal nerves without affecting the actual contents of the dentinal tubules (7). The problem with substances which merely raise the activation level of nerve endings (including corticosteroids) is that they do not strengthen the tooth and the pulp remains exposed to hydrodynamic irritation even after treatment. Consequently, the therapeutic effect of such treatment only lasts for a short time. Research results concentrating on the therapeutic effects of toothpastes are highly contradictory. On one hand, placebo effects, and on the other hand, pain relieving effects up to 80% have been reported. Generally, the problem with toothpastes is that they act very slowly, often only after several weeks of use. Thus, toothpastes may be suitable for home treatment of subacute problems. It is, however, necessary to find more powerful and quicker-acting methods for acute pain.

In clinical situations, today, the most common method for treating hypersensitive teeth is to use fluorides—either sodiumfluoride or tin fluoride in 2–10% mixtures (8, 9, 10). Fluoride can also be applied topically to the surface of a tooth in combination with varnish-based substances (Duraphat (11)). The varnish prolongs the effect of fluoride, and at the same time, the varnish itself may have some tubule blocking effect. At least over a short time-span, fluoride preparations have been shown to have positive therapeutic effects. Recently, some attention has been paid to the acidity of these preparations and irritation related to this acidity. It is thought, however, that problems caused by the acidity in the pulp can be relieved by alternating the use of calciumhydroxide and fluoride. This treatment has been empirical. In principle, results have been positive. Objective research data of the effects of the treatment or its permanence is not available. The presence of alkaline calciumhydroxide may, however, complicate the formation of the practically insoluble, and therefore, desired tinfluorophosphate; and instead, favour the formation of calciumfluoride which dissolves in neutral environment. In such conditions, the treatment may be effective, but temporary.

Solutions which assist the remineralisation of the tooth surface may also reduce sensitivity when used for long enough. Due to their watery nature and slow effect, this method—or those with the toothpastes—is not very good for the treatment of acute pain. For example, two mineralisation solutions—A and B—have been used. Solution A contains 6 MM $PO_4$ and B mM Ca. In addition, both solutions contain 0.15 mM NaCl and 5 ppm F. 10 ml of solution A and 10 ml of solution B are mixed in a glass immediately before use. The mixture of mineralisation solution, diluted in water is rinsed in the mouth for 1–2 minutes, and spat out. It is recommended that this procedure is repeated twice a day preferably after tooth brushing.

Potassiumoxalate ($K_2C_2O_4$ or $KHC_2O_4$, 3–30%) has also been used in the treatment of hypersensitive teeth. The idea behind the use of these chemicals as a therapeutical agent, is based on the ability of oxalate to precipitate calcium residing on the surface of a tooth or in the dentinal fluid. In this reaction, crystals which obstruct the transmission of hydraulic stimulus from the tooth surface into the pulp, are formed. A major part of the precipitate thus obtained usually dissolves within a week, but the diameter of dentinal tubules remain smaller than before treatment. Long-term effects of the treatment are still to be confirmed (3, 12, 13). More permanent results have been obtained with ferro-oxalate (6%) than with other oxalate treatments (14). At least one research report, however, has found acidic table salt solutions more effective than oxalate against hypersensitive teeth.

Products based on plastic polymers (resins, dentine adhesives) and cyanoacrylate effectively block dentinal tubules (15). At least over a short time-span, they remove pain and protect the pulp from the immediate irritation. These substances, however, cannot be regarded as biological, since they do not lead to a natural healing process and to the mineralisation of dentinal tubules. Dentine adhesives have also been found to be highly allergenic. The dental care personnel, however, are the major target of their allergenic effect. Additionally, acrylate, meta-acrylate and cyanoacrylate compounds have been found to be irritants, and also genotoxic and carcinogenic both in animal experiments and cell culture studies. Plastic-based "coating" also forms a microbe retentive surface at the area of gingiva-tooth junction which easily leads to the recurrence of the recently treated disease. Thus, the use of dentine adhesives, especially in periodontal patients, cannot be regarded as meaningful. When considering filling materials, glass ionomer cement has also been proposed for the treatment of hypersensitive teeth (11). Advantages of glass ionomer cement are its properties to bind dentine and to release fluoride. In practice, glass ionomer cement is difficult to use, especially in the treatment of widely exposed dentine.

However, it is suitable for the treatment of distinctly defined and relatively deep abrasion lesions which are found clearly above the gingiva margin.

Older literature suggests that dentinal tubules should be blocked by using silver nitrate. The results of using this substance have been highly variable. In addition, silver nitrate is a highly staining agent. The treatment of root surfaces first with zinc chloride and then with potassium ferrocyanide have also been proposed. The treatment yields a protective precipitate on the surface of a tooth. The results have been reported to be satisfactory. If swallowed by mistake, however, the agent is toxic.

The use of a NdYAG laser has been proposed as a potential new approach for closing the dentinal tubules. Preliminary results with this treatment are promising. The mechanism behind the treatment, the permanence of the treatment and its possible adverse effects on the pulp are still to be confirmed.

The heterogeneity of possible treatments presented above, gives a good picture of a dentist's real and realistic choices in the effective treatment of hypersensitive teeth. Even after several years of experiments, none of the offered alternatives has proved to be any better than the other, and thus a predominant method of treatment. Common to all the offered methods, is that they do not consciously aim at producing an apatite-based compound ($Ca_{10}(PO_4)_6X_2$, in which X is either a hydroxyl or fluoride)—chosen by nature—to close the dentinal tubules. Generally, the goal has been to make any type of precipitate to block the dentinal tubules as quickly as possible (3, 16, 17). None of the tested methods of treatment has aimed at contributing to the crystallisation process itself, by simultaneously adding calcium and/or phosphate which essentially participates in the formation of precipitate/crystals. Therefore, at the background of the partly contradictory results reported may be the availability of these essential ions during the short period of treatment. On the other hand, some of these treatments have sought results through the cumulative effects of short-term application (e.g. toothpastes and remineralisation solutions). An exception to these treatment concepts is the use of fluoride containing preparations, although their effect is not based on increasing the availability of calcium or phosphate on the area to be treated.

The purpose of the present invention is to eliminate the above mentioned problems and present a new, effective preparation for reducing or inhibiting pulpal irritation i.e. hypersensitivity of a tooth. The preparation also provides a new method for effectively strengthening a tooth.

BRIEF SUMMARY OF THE INVENTION

This invention concerns a novel use of bioactive silica containing glass for making a preparation which reduces pulpal irritation and/or strengthens the tooth structure. This invention also concerns a pharmaceutical preparation which reduces pulpal irritation and/or strengthens the tooth structure. The preparation comprises a glass phase, which is bioactive silica containing glass in the form of a paste, suspension or solution in a physiologically suitable liquid, or bound to a physiologically suitable vehicle such as fibrinogen or chitin.

DETAILED DESCRIPTION OF THE PREFERRED EMBODIMENTS

In the following, the term "bioactive silica containing glass" refers to a material comprising Si-oxide or Si-hydroxide wherein said material allows the formation and movement of Si—OH-groups. The bioactive silica containing glass may be, for example, either 1) bioactive glass, which refers to a mixture of Si-oxide or Si-hydroxide with one or more elements, the elements being: sodium, potassium, calcium, magnesium, boron, titanium, aluminium, nitrogen, phosphorous and fluoride; 2) water glass type sodium silicate; 3) silica gel i.e. Si-hydroxide; 4) solution comprising Si—OH groups; 5) silica gel comprising Ca, P or 6) hydroxyapatite comprising Si-oxide or Si-hydroxide. It is essential that bioactive silica containing glass allows the formation and movement of Si—OH groups. It is recommended that the bioactive silica containing glass also allows the formation and movement of calcium and phosphate ions.

Figure 1:
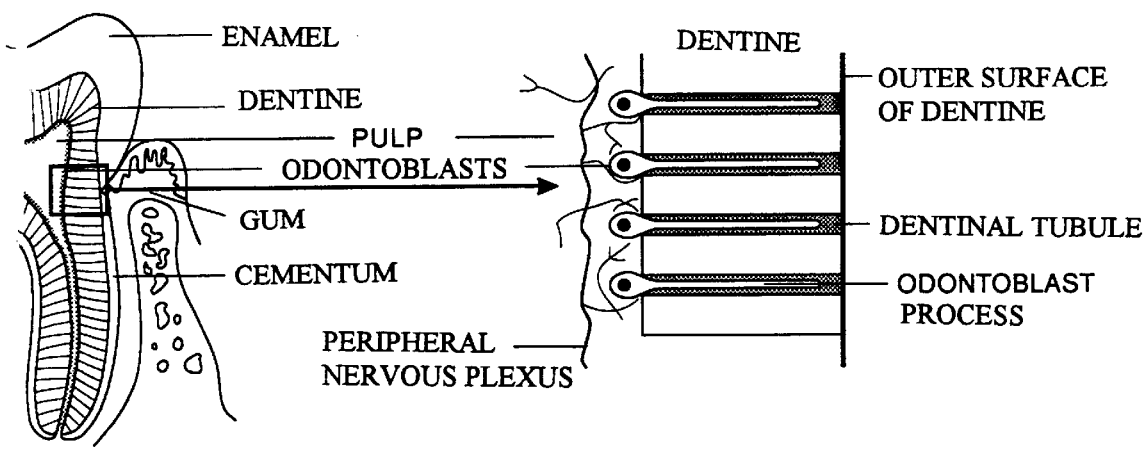
FIG. 1 shows the structure of dentine.
Figure 2:
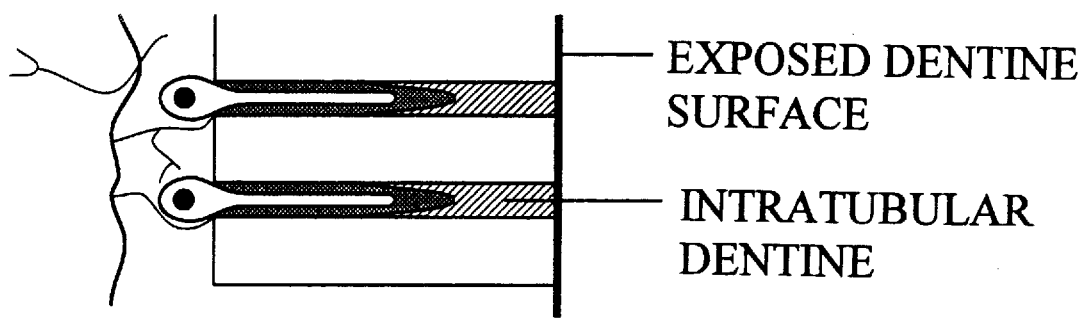
FIG. 2 depicts gradual closing of the tubules around receding odontoblast processes.
Figure 3:
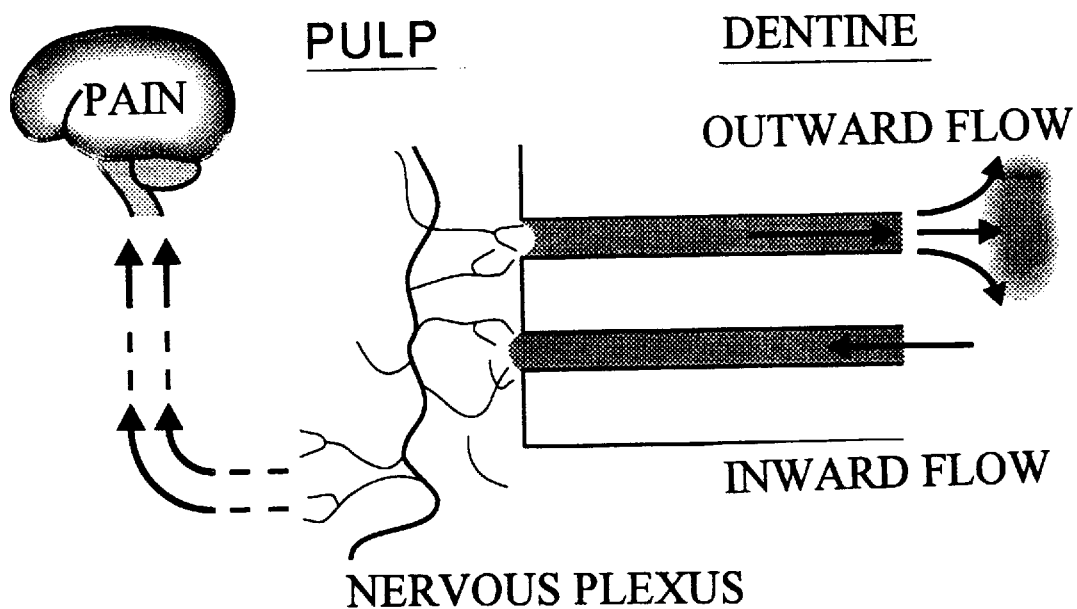
FIG. 3 illustrates a dental pain transmission mechanism.
Figure 4:
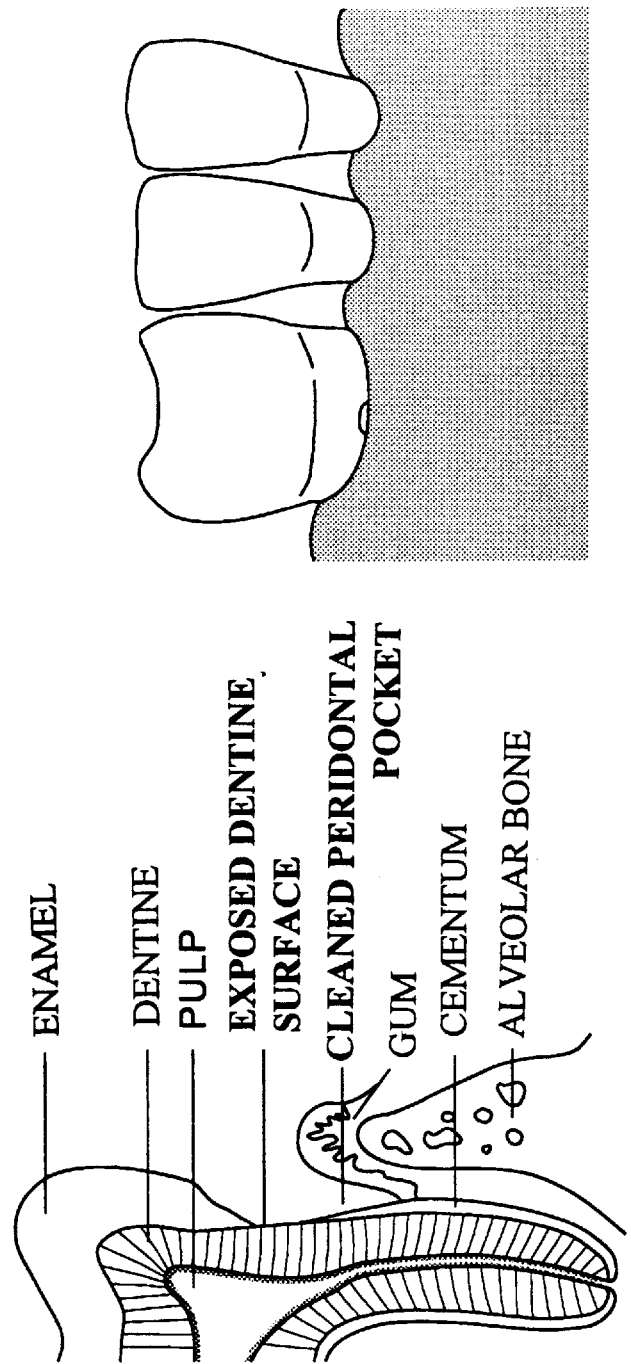
FIG. 4 shows a tooth having an exposed dentinal surface.
Figure 5:
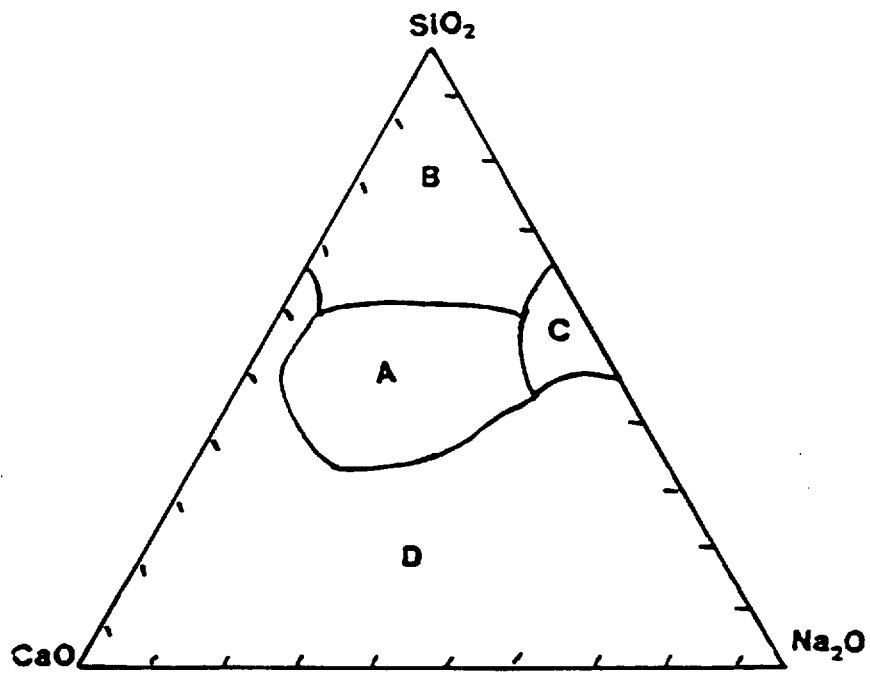
FIG. 5 is a ternary phase diagram of the bioactive area of certain oxide mixtures.

FIG. 5 illustrates a ternary phase diagram of the bioactive area of certain oxide mixtures. In addition to $SiO_2$, CaO and $Na_2O$, the mixture can, of course, include oxides together with the elements mentioned in the previous paragraph. Some of the typical bioactive glass compositions are presented in Table 1.

TABLE 1

Composition (weight %) of some bioactive glass types 1–10.

| Glass | Type | $Na_2O$ | CaO | $P_2O_5$ | $B_2O_3$ | $Al_2O_3$ | $SiO_2$ |
|---|---|---|---|---|---|---|---|
| 1 | S57.5P5 | 16.00 | 18.00 | 5.00 | 3.00 | 0.50 | 57.50 |
| 2 | S56P6 | 19.00 | 16.00 | 6.00 | 1.50 | 1.50 | 56.00 |
| 3 | S51P7 | 20.00 | 17.00 | 7.00 | 3.00 | 2.00 | 51.00 |
| 4 | S53P4 | 23.00 | 20.00 | 4.00 | 0.00 | 0.00 | 53.00 |

TABLE 1-continued

Composition (weight %) of some bioactive glass types 1–10.

| Glass | Type | Na$_2$O | CaO | P$_2$O$_5$ | B$_2$O$_3$ | Al$_2$O$_3$ | SiO$_2$ |
|---|---|---|---|---|---|---|---|
| 5 | S45P7 | 24.00 | 22.00 | 7.00 | 2.00 | 0.00 | 45.00 |
| 6 | S52P8 | 25.00 | 12.00 | 8.00 | 0.50 | 2.50 | 52.00 |
| 7 | S46PO | 26.00 | 25.00 | 0.00 | 2.00 | 1.00 | 46.00 |
| 8 | S38P8 | 27.00 | 23.00 | 8.00 | 1.00 | 3.00 | 38.00 |
| 9 | S48P2 | 28.00 | 19.00 | 2.00 | 1.50 | 1.50 | 48.00 |
| 10 | S55.5P4 | 29.00 | 11.00 | 4.00 | 0.00 | 0.50 | 55.50 |

Bioactive silica containing glass is used in the preparation in the form of a powder suspended in a physiologically suitable liquid or is bound to a physiologically suitable vehicle. The preparation should be sufficiently moist so that chemical interactions between the glass phase and dentine are maintained.

The glass phase of the preparation may consist solely of Si-oxide or Si-hydroxide, such as silica gel. Alternatively, in addition to Si-oxide or Si-hydroxide, the glass phase may include one or more of the following elements: Ca, P, Na, K, Al, B, N, Mg, Ti or F.

The suitable composition of a glass phase could be as follows:

| | |
|---|---|
| SiO$_2$ or Si-gel | 1–100% |
| CaO | 0–40% |
| P$_2$O$_5$ | 0–60% |
| Na$_2$O | 0–45% |
| K$_2$O | 0–45% |
| MgO | 0–40% |

Although silica gel or water glass type of alkali containing silicate glass can induce the mineralisation of dentine with the help of the calcium and phosphate present in the body fluids, it is advisable to use such bioactive glass compositions which comprise calcium and phosphate. Alternatively, calcium and phosphate containing sources, such as ceramic powder can be added in the preparation.

Suitable binding agents are, for example, fibrinogen or chitin.

The preparation can also comprise substances which promote crystallisation, such as TiO$_2$. Agents assisting crystallisation refer to the agents which contribute to the formation of a crystal or assist in increasing their size.

Figure 6:
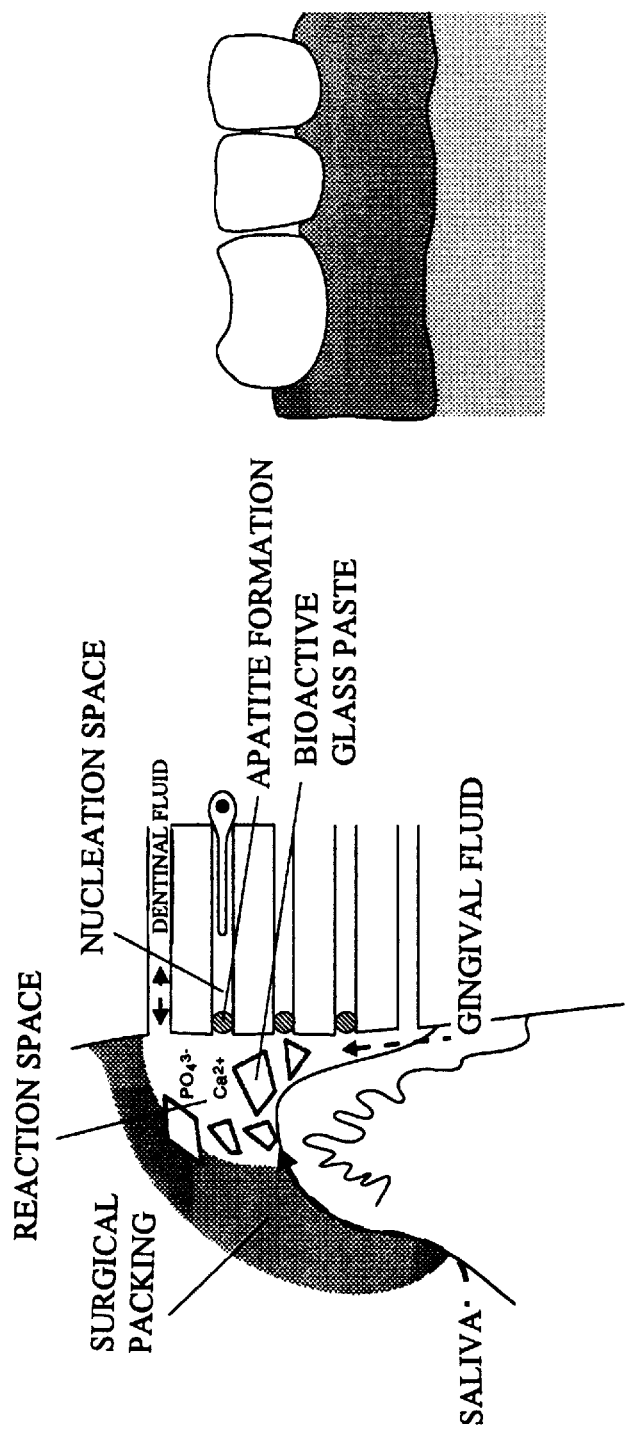
FIG. 6 illustrates the application of a preparation containing bioactive silica containing glass against the dentine surface.

The preparation is placed in contact with the surface of a tooth, in a periodontal pocket, in a drilled cavity or on a polished surface or otherwise exposed dentinal surface, by covering the area locally or widely with the said preparation. The preparation can then be covered with a protective packing, cementum or with some other corresponding method which prevents the displacement of the preparation. FIG. 6 presents the application of a preparation against the dentine surface.

Figure 7:
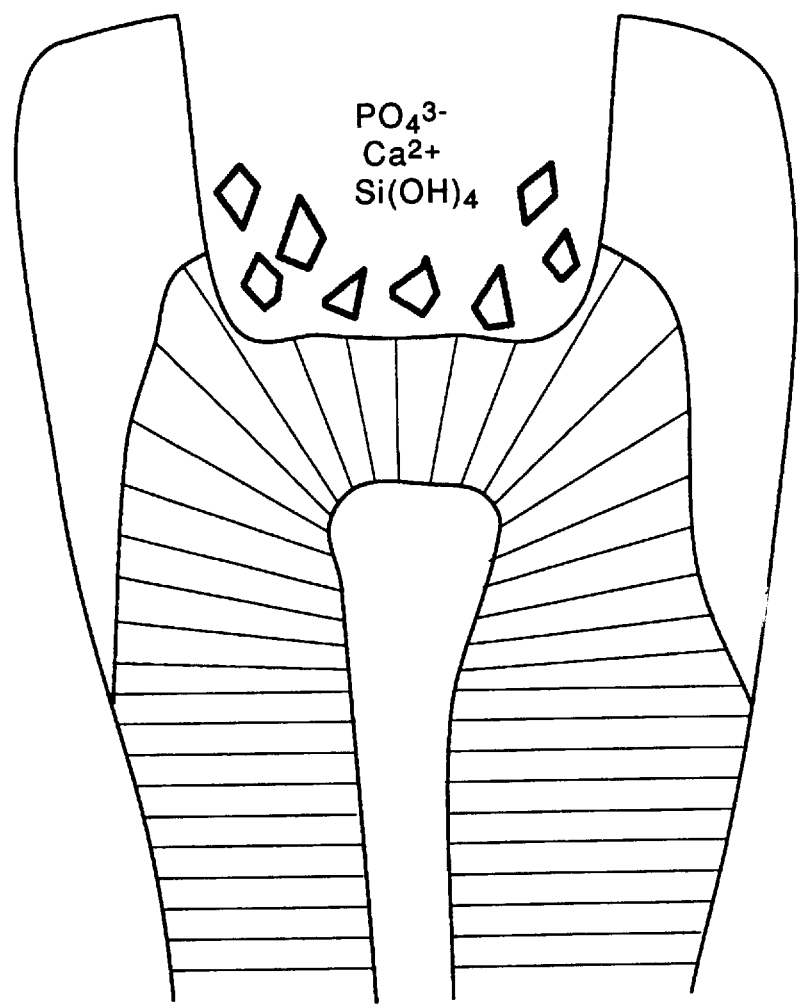
FIG. 7 depicts filling the bottom of a cleaned cavity with a preparation containing bioactive silica containing glass.

A few embodiments of the invention are presented in the following:

When making a temporary filling, it is possible to mineralise (sclerotise) the dentine tubules, by filling the bottom of the cavity cleaned from caries with the bioactive silica containing glass (FIG. 7) according to the method presented in this invention. The remaining hard tissue layer will be strengthened and possible pulpal irritation, caused by the permanent filling or its preparation, is reduced. In other words, the tissue layer strengthened with the method described in this invention also serves as an insulating layer. In cases of non-existent or very thin dentine layer, the glass acts as a bioactive surface which favours the formation of secondary dentine. In addition, well mineralised dentine is more resistant to new caries attacks than less mineralised dentine.

Figure 8:
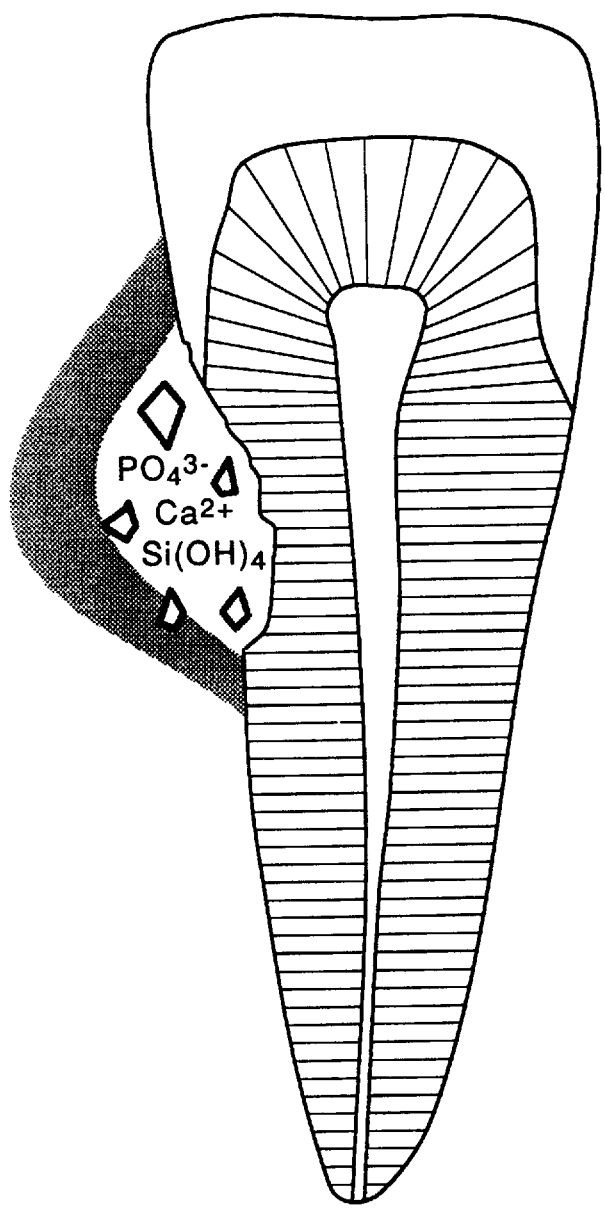
FIG. 8 shows the application of a preparation containing bioactive silica containing glass against an eroded surface of a tooth.

The erosion of a tooth refers to a phenomenon in which the surface of a tooth is dissolved by acids which are not produced by bacteria as in the case of caries. Such acids enter the mouth if gastric juice frequently rises to the oral cavity (e.g. acidic burps and bulimia). This may also happen, for example, in the case of heart burn (ulcer), if one eats a lot of citrus fruit and drinks acidic wine or sports drinks. In such situations, the surface of a tooth quickly erodes (FIG. 8) and the tooth becomes hypersensitive. By treating the primary disorder and surfaces according to the method of the present invention, two benefits are obtained: hypersensitivity is eliminated and the dentine becomes more resistant to new acidic attacks because of its higher degree of mineralisation. Since the screlotisation of dentine strengthens the tooth against mechanical wear, too, the preparation of this invention can be used for treating other types of attrition damages, for example, those caused by wrong toothbrushing habits.

Figure 9:
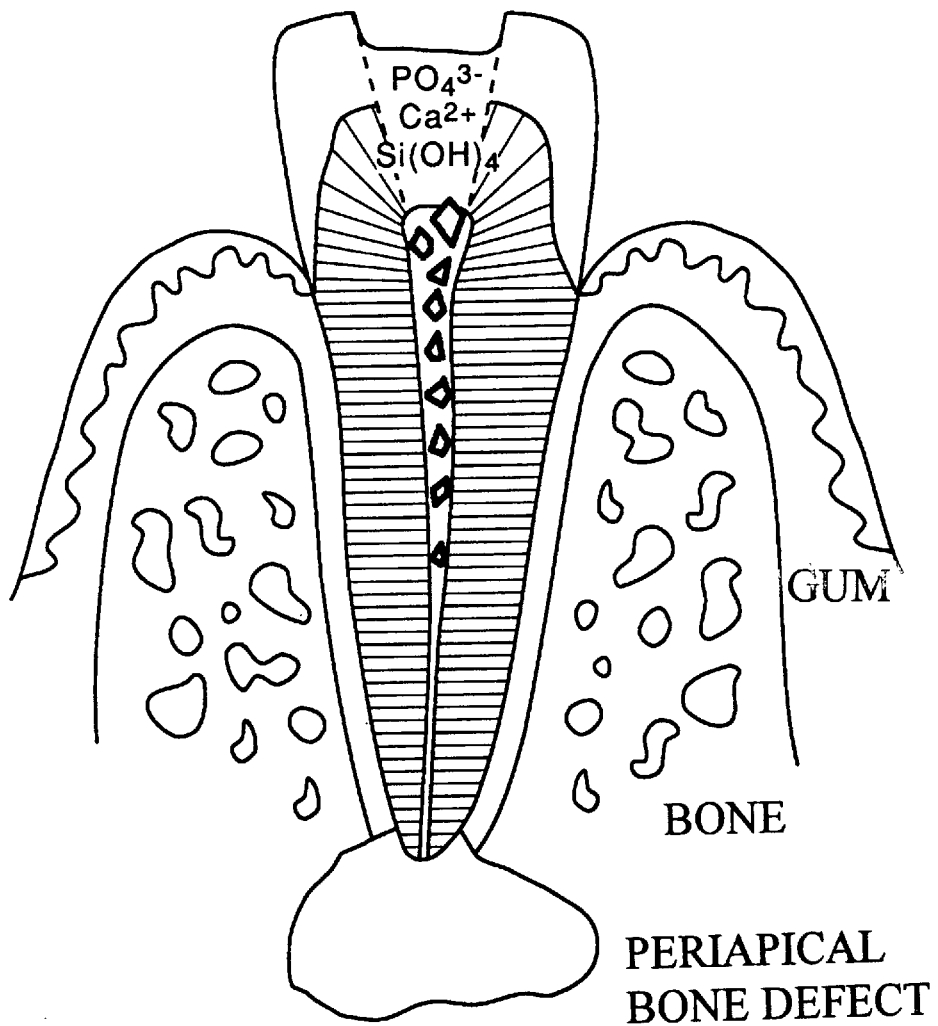
FIG. 9 illustrates filling an empty root canal with a preparation containing bioactive silica containing glass to strengthen the tooth by mineralization of the dentinal tubules.

In teeth which require root canal treatment, the pulp is dead and nearly always infected, which results in the destruction of the bone surrounding the apex of the tooth's root. With proper treatment, it is possible to keep this kind of a tooth functional. The tooth is, however, more fragile than a healthy tooth and it cracks and even breaks easily. By filling the empty root canal temporarily with the glass paste/suspension of this invention before the final filling, it is possible to mineralise the dentinal tubules and strengthen the tooth (FIG. 9). At the same time, the method creates a favourable environment for the healing process of the bone at the apex of the root.

Figure 10:
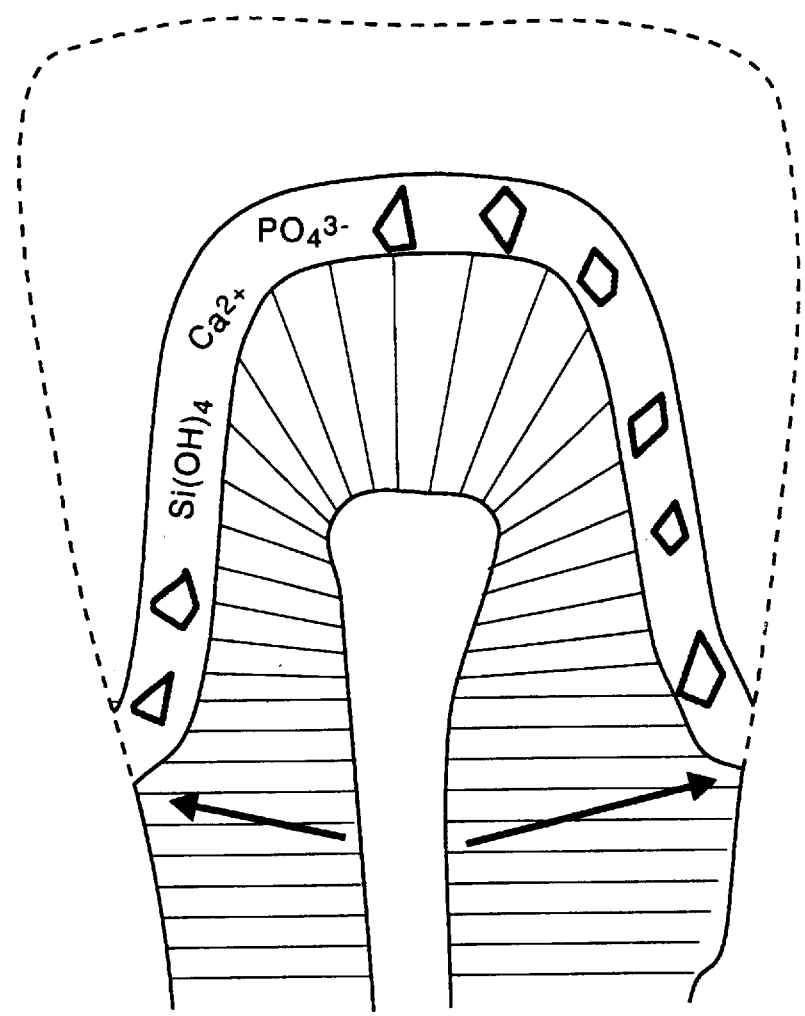
FIG. 10 depicts the placement of a temporary crown using bioactive silica glass containing paste as a binding agent.

In the crown prosthetics, a tooth is trimmed into the shape of a conic pillar, on top of which a crown is fitted. During the trimming process, a huge number of dentinal tubules is exposed, which results in highly sensitive teeth until the work is completely finished. The trimmed teeth are covered with temporary crowns during the process. Temporary crowns can be fixed into place using bioactive silica glass containing paste as a binding agent (FIG. 10.). The benefits are the same as with the restorations. The pillar becomes stronger, hypersensitivity problems disappear, and when finished, the dentine at the edges of the prosthetic crown is less susceptible to caries.

The obtained clinical effect is based, firstly, on the fact that the preparation induces crystallisation of apatite in the dentinal tubules of a tooth; and secondly it promotes dentine formation as a result of the induction of odontoblast activity.

From the standpoint of desired action, it is preferrable that the high calcium and phosphate ion concentration is maintained in close vicinity to the dentinal tubules long enough to ascertain that the ions are diffused into the tubules as deep as possible. Actual precipitation/crystallisation is induced by a factor, called a nucleator, which lowers the energy barrier preventing the crystal formation and initiates the natural closing process of dentinal tubules. In the present invention, the nucleator, as well as the ions contributing to the composition of the precipitate and the crystal size, are brought from outside by keeping the active silica containing glass in contact with the tooth.

Nucleation

Mineralisation as a biological phenomenon is complex and difficult to control. To understand its fundamental mechanism, mineralisation is a target of intensive and continuous study. One of the basic features relating to mineralisation, is that although serum and tissue fluids are supersaturated solutions with regard to calcium and phosphate, spontaneous crystallisation does not take place in tissues. Thus, for example, tissue fluid or other solutions with equivalent concentrations of calcium and phosphate can be kept in a test tube for an endlessly long time without any crystal formation. If a tiny crystal of hydroxyapatite is then added into the test tube, the crystal starts to grow at the expense of the calcium and phosphate in the solution. Crystallisation is not initiated without assistance because the condensation of the ion clusters, which is the prerequisite for the formation of a crystal nucleus, requires energy as chemical reactions generally do. Crossing the threshold requires special conditions and/or an outside factor (nucleator).

In principle, the initiation of crystallisation, i.e. the formation of an crystal nucleus, can be assisted in three ways:

1) The amount of inorganic ions can be increased, so that a certain critical number of ion clusters are formed locally and simultaneously in a small space. Under these conditions, the energy threshold preventing the condensation of any of the ion clusters may be crossed. The formed crystal nuclei progresses the crystallisation either by growing in size itself or acting as a nucleator for the other still labile ion clusters around it (secondary nucleation). If the crystal formation is initiated as described above, it is called homogenic nucleation.

2) With the presence of a factor (nucleator) which lowers the energy threshold preventing the formation of a crystal nucleus, it is not necessary to increase ion concentration. If the crystal formation is initiated with the help of an outside nucleator, it is called heterogenic nucleator.

3) There are also agents which raise the energy threshold thus preventing the formation of a crystal nucleus. One of the most well-known of these agents is pyrophosphate. Consequently, the removal or inactivation of such a locally-acting inhibitor may assist mineralisation.

Once a crystal nucleus has formed, it continues to grow so that new ions continuously diffuse from the solution onto the surface of the crystal. In a normal biological environment, the mineralisation of connective tissue also involves cell activity. The cells build a mineralisation frame formed by the extra cellular matrix. At least at the beginning of the mineralisation process, small membrane lining structures (matrix vesicles) can be seen on the surfaces of the cells forming hard tissue. The vesicles contain calcium binding lipids and alkaline phosphatase. It is thought that it is specifically these conditions that are especially favourable for the formation of the first crystal nuclei. Once the crystal nucleus has formed, the vesicle bursts and the crystal leaves the interior of the cell and becomes a building block for hard tissue. Since these vesicles only appear at the beginning of the hard tissue formation, it is apparent that there must also be other mechanisms which lead to the mineralisation of a tissue. In fact, the extracellular matrix contains quite a few organic molecules which may act as nucleators, at least, in vitro. These molecules include, for example, osteonectin, phosphoproteins, collagen, anionic phospholipids and sulphur containing compounds such as chondroitinsulphate and ceratansulphate.

Alkaline phosphatase is always found where hard tissue is formed. Its role in the formation of hard tissue is not completely clear. It is obvious, however, that it is an enzyme, which in the alkaline environment participates both in the hydrolysation of different organic compounds and in the release of phosphate ions.

Intratubular dentine does not contain an actual mineralisation frame (organic matrix). This is shown when demineralised tooth samples are prepared and dentinal tubules appear hollow at those sites which were filled with intratubular dentine. This does not exclude, however, the involvement of nucleators in the mineralisation of intratubular dentine. The situation appears to be just the opposite, because odontoblasts and/or their processes are known to respond to certain stimuli and are able, at least to some extent, to accelerate the formation of protective intratubular dentine. It is also possible, however, that the primary stimulus does not stimulate cell activity, but is sufficient to initiate the degeneration of a cell. Consequently, parts of a degenerating cell may act as nucleators. The latter case is, at least partly, indicative of a pathological phenomenon. The third alternative is that certain components of the tissue fluid flowing into the dentinal tubules act as nucleators. This kind of a situation is created, for example, when the cementum layer of the root surface is removed during the treatment of periodontitis and the dentinal tubules are exposed as a wound-resembling surface with open connections to the pulp of the tooth.

Silica as a Nucleator

The dissolution of silica from the glass type used in the examples is minimal when the pH of the surface is below 9. Above this value, its dissolution increases significantly, and is dominant when the pH exceeds 9.5. A characteristic feature of active glass is that as it increases the pH in its surroundings, its $Si(OH)_4$ molecules begin to dissolve. It is clear that when using small granule size in a limited reaction space, the pH becomes quite high which, in turn, results in an abundant release of silica. In a biological environment, silica also spreads out into tissues.

The Ca,P layer precipitating on the surface of the glass is rich in silica over the whole precipitation area. This suggests that silica has an active role in the formation of the precipitate. Because silica spreads out into the tissues, it may act as a nucleator also there. On the other hand, in many organic systems, where glass is one of the components, the ability of collagen to act as a nucleator for apatite crystals is important.

Figure 11:
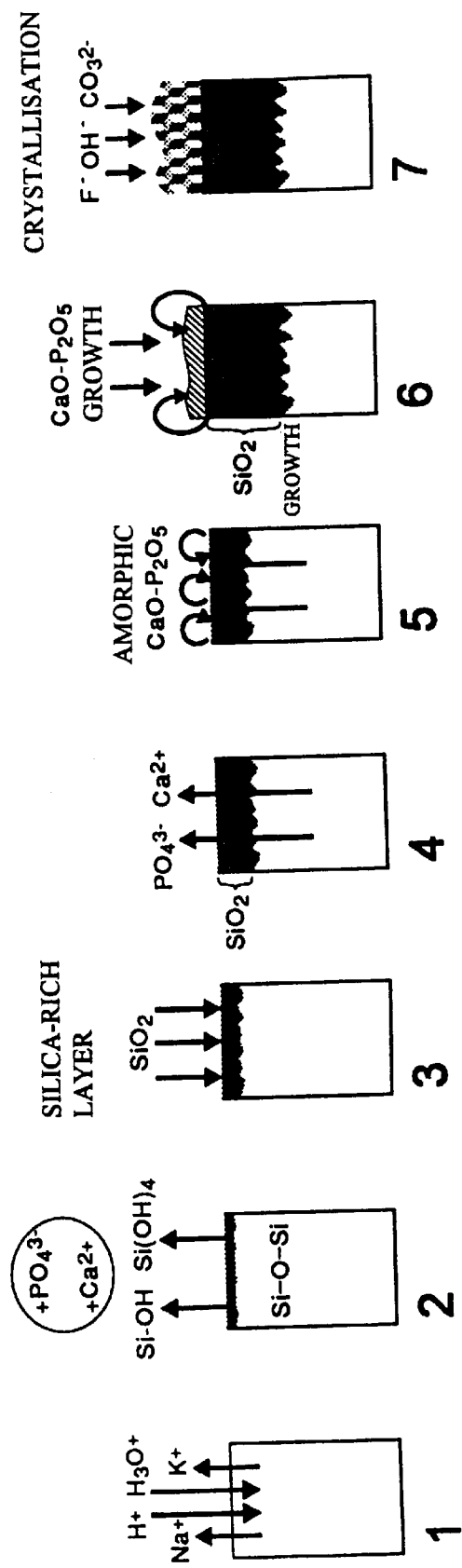
FIG. 11 shows the reactions which occur on the surface of the bioactive glass.

When glass comes into contact, for example, with body fluids, the surface reactions of the glass are induced by a quick ion exchange as the hydrogen ions and $H_3O^+$ ions in the body fluids diffuse onto the surface of the glass, and the alkaline $Na^+$ and $K^+$ ions, in turn, are released from the glass. The network formed by the Si—O—Si bonds of the glass are broken, but may, if pH is below 9.5, immediately repolymerise into a silica-rich, gel-like layer on the surface of the glass. In such a situation, however, the silica is also always dissolved. If pH is above 9.5, the dissolution is complete. The pH of the surrounding liquid has a strong effect on ion exchange. Low silica content of the glass and open structure formed by the silica atom network, promote rapid exchange of ions. The calcium and phosphate ions in the glass are diffused through the silica-rich layer; and, they first form an amorphic calciumphophate layer on top of the silica-rich layer. These reactions are initiated within a few minutes when the glass is brought into contact with the liquid. During the days that follow, the silica-rich layer and calciumphosphate layer become gradually thicker. At the same time, amorphic calciumphosphate starts to crystallise into apatite. The formed apatite layer is rich in silica. This is an indirect proof that, in an inorganic system formed by glass and liquid, it is the silica which acts as a nucleator for crystal formation. The above mentioned reactions on the surface of the bioactive glass are illustrated in FIG. 11.

The present invention is described in more detail in the following examples.

EXAMPLE 1

$SiO_2$ (Belgian sand), $Na_2CO_3$, $CaCO_3$ and $CaHPO_4H_2O$ were mixed in the desired proportion and poured into a platinum crucible. The crucible was placed into the oven at 1360° C. After three hours, the crucible was taken out of the oven and the melted composition was poured into clean water. The composition of the resulting crushed glass was equivalent to composition number 4 (S53P4) in Table 1. The glass was immediately removed from the water and rinsed with alcohol. The glass was ground into a fine powder in a ball mill and sifted. Particles below 45 micrometers were collected for future use. The produced glass powder was used in the preparation described in the present invention as follows: the glass powder (1.2 g) was suspended in water (0.4 g) before its application onto the surface of the root of a tooth.

EXAMPLE 2

The glass powder (S45P7), the composition of which was equivalent to number 5 in Table 1, was prepared. The same raw materials and methods as in Example 1 were used in the preparation with one exception: the melting time was 2.5 hours at 1340° C. The prepared glass powder was suspended in a physiological saline solution before use.

EXAMPLE 3

The glass powder (S46PO) of composition number 7 in Table 1 was prepared as described in Example 2. This composition does not contain phophate. The prepared glass powder was suspended in a physiological saline solution before use.

EXAMPLE 4

The composition described in Example 3 was modified so that $Al_2O_3$ was replaced with an equivalent amount of $SiO_2$. Otherwise, the glass powder was prepared as described in Example 3. This composition released silica more rapidly than the composition in Example 3. The prepared glass powder was suspended in a physiological saline solution before use.

EXAMPLE 5

Sodiumsilicate glass powder was prepared according to the method described in Examples 1–4. $SiO_2$ and $Na_2CO_3$ were used as raw materials and the glass was melted for 3 hours at 1350° C. The prepared glass powder was suspended in water before use.

EXAMPLE 6

A commercial water glass, i.e. sodiumsilicate solution, was used as such in the preparation of the present invention.

EXAMPLE 7

A commercial water glass was neutralised with hydrochloric acid. The formed Si-gel was washed with ion-changed water. The Si-gel was dried and the powder was suspended in water before use, as described in Example 1.

EXAMPLE 8
Preliminary Clinical Experiment

Figure 12:
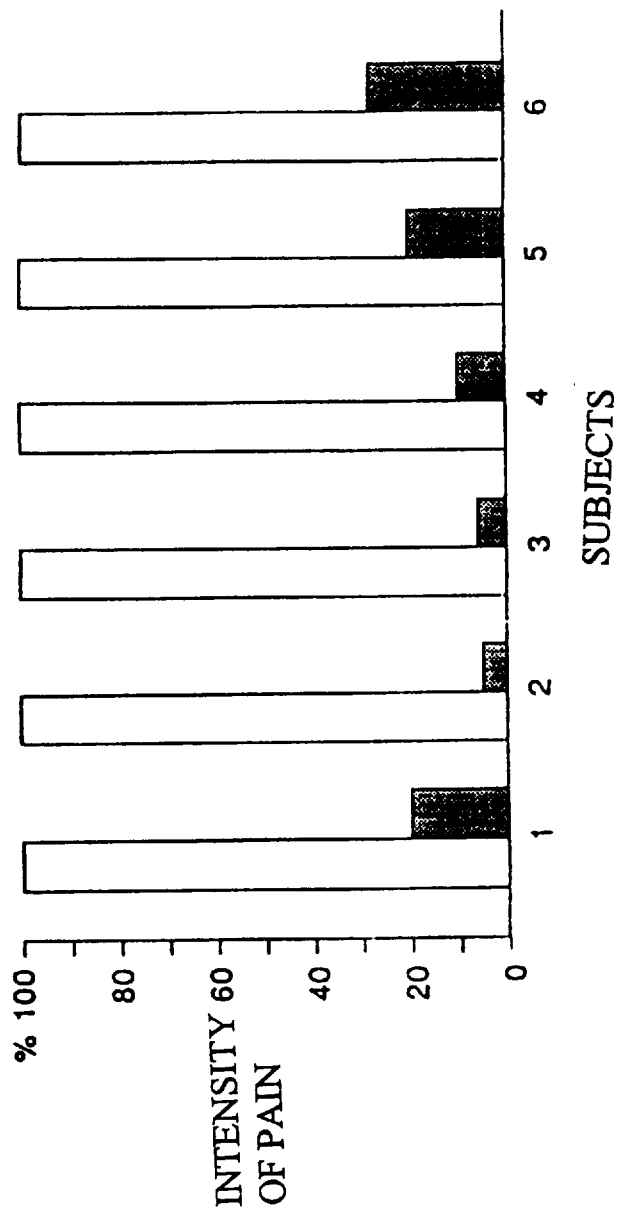
FIG. 12 is a graph of subjective estimation of pain of patients after an initial treatment of bioactive silica containing glass to tender and hypersensitive dentine.

Six people (5 women and 1 man), with an average age of 51, participated in the experiment. Four subjects had recently undergone a periodontal flap surgery. All six subjects suffered from tender and hypersensitive dentine. A total of 19 teeth were treated. A bioactive glass powder (S53P4; Table 1; maximum particle size 45 µm) was mixed in a physiological saline solution to form a suspension/paste immediately before use as described in Example 1. The areas to be treated with the preparation were washed and dried carefully. The paste was spread over the area with a foam pad to form a fairly thick layer. The area was covered with a surgical packing (Coe-Pak) for a week. Patients' subjective sensations of pain, measured by using a visual analoque scale (VAS) immediately after the treatment period, was used to assess the reduction of pain. Pain was triggered by using a blast of air and scraping with a probe. The degree of pain was measured at one end of the scale as severe pain and as no pain at the other end of the scale.
Results FIG. 12 shows the subjective estimation of pain after the initial treatment. For all the patients, the pain practically vanished after one single treatment. The treatment was repeated for two subjects, after which neither of the patients experienced pain when the tooth surface was probed or air blast. One patient returned for a post-control check after 3 months. She experienced no more hypersensitivity.

EXAMPLE 9

Small samples extracted from the gingiva in connection with tooth exposure operations, performed on young patients were cultured on a bioactive glass substratum, S53P4. Generally, the tissue samples were found to grow well on the surface of the glass and the tissue culture technique was suitable for studying reactions between bioactive glass and different types of soft tissue. The advantages of tissue cultures are that it is possible to study the reactions of both epithelium and connective tissue simultaneously. When the samples were examined electronmicroscopically, epithelial cells were discovered to have formed an organic attachment i.e. hemidesmosomes, and a structure resembling a basal lamina, against the surface of the glass.

This experiment, published earlier (18), showed that epithelial tissue accepts bioactive glass and adheres to it.

EXAMPLE 10
CaP-Precipitatations Found in Cultured Connective Tissue in Vitro

The tissue cultivation was performed as described in example 9.

Figure 13:
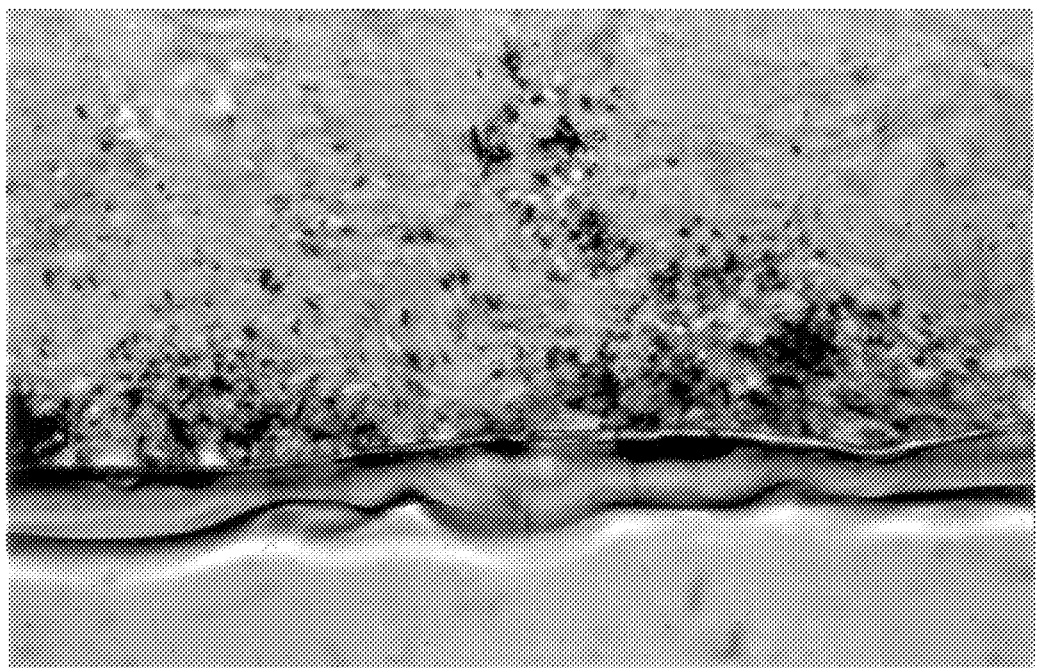
FIGS. 13 and 14 are scanning electron micrographs of cultured connective tissue in vitro which show collagen fibrils of connective tissue trapped inside the apatite layer growing on the surface of the glass.
Figure 14:
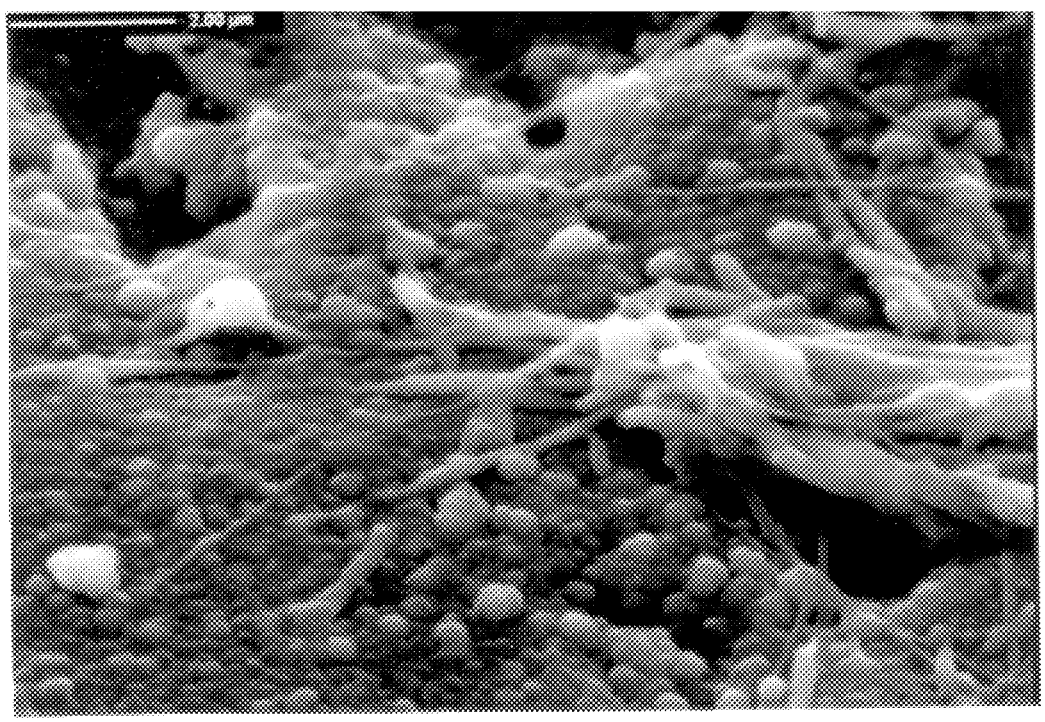

Von Kossa staining, which stains the calcium salts, revealed CaP-precipitation extending from the surface of the glass, deep into the connective tissue when examined under the light microscope. Analysis of the sample with a scanning electronmicroscope confirms the histological finding: collagen fibrils of connective tissue are trapped inside the apatite layer growing on the surface of the glass (FIGS. 13 and 14).

The element analysis of the samples also shows that Si-ions diffuse deep into the connective tissue.

EXAMPLE 11

In Vitro Experiments on Decalcified Dentine

Figure 15:
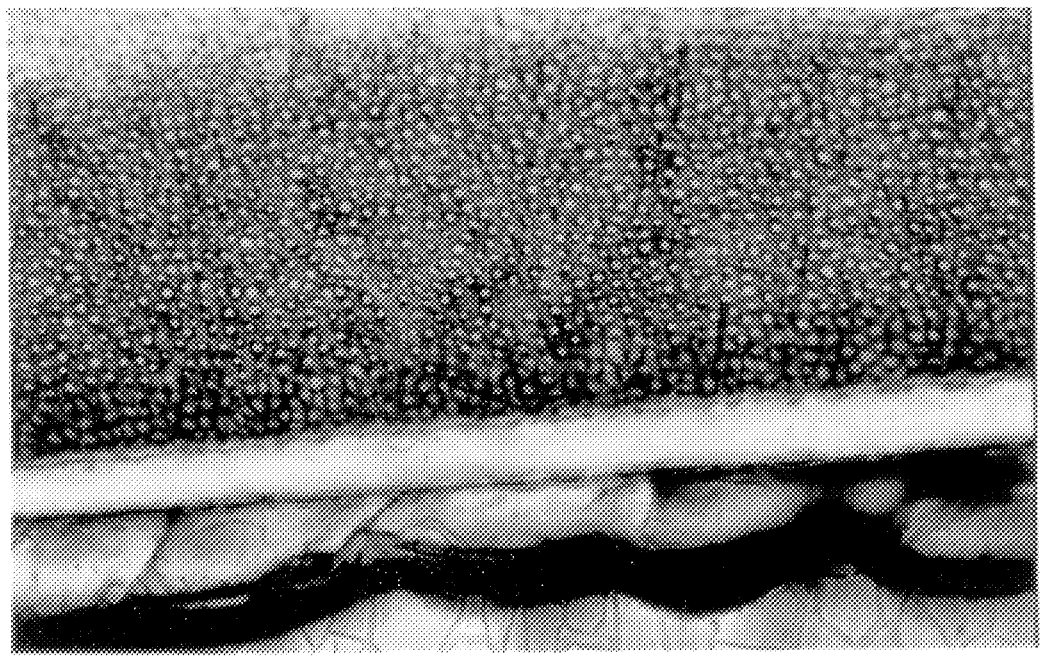
FIGS. 15 and 16 are light micrographs which show fully mineralized dentinal tubules near the surface of the glass.
Figure 16:
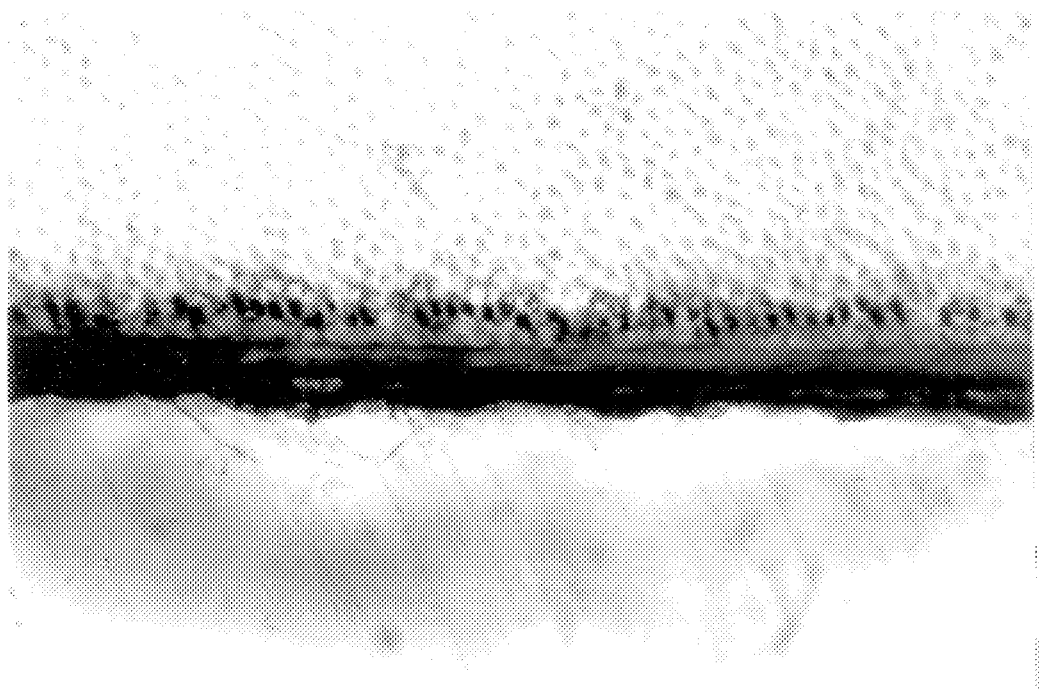

An extracted tooth was sliced into 200 µm thick sections and treated with hydrochloric acid to dissolve the inorganic components. Dentinal tubules became open as the highly mineralised intratubular dentine dissolved away. The remaining matrix was soft and contained nearly pure Type I collagen, the same as, for example, the connective tissue of the oral mucosa. By using the tissue culture technique described in Example 9, dentine was incubated for 5 days in the culture. The glass (S53P4) and collagen were not found to adhere to each other, but as the collagen sample was bent manually, it felt rigid, as did the dentine section before the acid treatment. When studied under light microscope, it was discovered that the section had remineralised at the depth of 100–150 μm. The dentinal tubules near the surface of the glass, were fully mineralised (FIGS. 15 and 16).

This experiment shows that bioactive silica containing glass acts as a vehicle which can be used to mineralise collagen structures and close the dentinal tubules in the dentine. The experiment clearly shows that it is possible to strengthen tooth tissue with the preparation according to the present invention when it is used in association with root canal therapy and filling of a tooth. The experiment further shows that with the help of the preparation of the present invention, it is possible to harden collagen and prepare an agent suitable for a bone substitute or for another type of preparation which can be implanted in living tissues.

EXAMPLE 12
In Vivo Experiments in Rats

Experimental periodontal bone defects were made palatally beside the molars in upper jaws of rats. Bioactive glass (composition=S53P4 in Table 1) powder (granule size 250–315 μm) mixed in a saline solution was applied to one side of the jaw, the other side serving as a control. To initiate the healing process of the bone defect, bioactive glass was allowed to act for 3 weeks. Soft tissue appeared to be similar both on experimental and control sides. Epithelium readhered onto the surface of the tooth, and connective tissue did not show infiltration of inflammatory cells. The material was found to be biocompatible at this location.

This experiment demonstrated tissue compatibility of the material in vivo.

It will apparent to the experts in the field that the embodiments of the present invention may take different forms in the scope of the claims presented hereinafter.

List of References:
1. Närhi, M. V. O., *Dent. Clin. North. Am.* 1990, 34:439–448.
2. Kontturi-Närhi V. Dentine hypersensitivity—factors related to the occurence of pain symptoms. Thesis 1993.
3. Greenhild J. D. & Pashley D. H., *J. Dent. Res.* 1981, 60:686–698.
4. McFall W. T. & Morgan W. C., *J.Periodontol.* 1985, 56:288–292.
5. McFall W. T. & Hamrick S. V., *J.Periodontol.* 1987, 58:701–705.
6. Addy M. et al., *Br. Dent. J.* 1987, 163:45–51.
7. Chesters R. et al., *J. Clin. Periodontol.* 1992, 19:256–261.
8. Krauser J. T., *J. Prosthet. Dent.* 1986, 56:307–311.
9. Kern D. A. et al., *J. Periodontol.* 1989, 60:386–389.
10. Squillaro R. et al., *J. Dent. Res.* 1981, 60:461.
11. Hansen E. K., *Scand. J. Dent. Res.* 1992, 100:305–309.
12. Pashley D. H. & Galloway S. E., *Arch. Oral. Biol.* 1985, 30:731–737.
13. Kerns et al., *J. Periodontol.* 1991, 62:421–428.
14. Salvato A. et al., *J. Dent. Res.* 1990, 69:169.
15. Swift E. J. et al., *Jada Vol.*125, 1994, 571–576.
16. Hiatt W. H. & Johansen E., *J. Periodontol.* 1972, 43:373–380.
17. Imai Y. & Akimoto T., *Dental Material Journal* 1990, 9:167–172.
18. Tuominen U.I. et al., *Bioceramics Vol.* 6, 1993, pp. 151–156.

We claim:

1. A method of treatment of a person suffering from pulpal irritation and/or in need of strengthening his tooth structure, comprising treating at least one tooth of said person with a preparation consisting essentially of bioactive silica containing glass, wherein said preparation is capable of rapid release of silica in a concentration effective to induce crystallization of apatite in dental tubules and/or on the tooth surface.

2. The method of claim 1, wherein said bioactive silica containing glass is in the form of a powder suspended in a physiologically acceptable liquid, or is bound to a physiologically acceptable binder selected from the group consisting of fibrinogen and chitin.

3. The method of claim 1, wherein said bioactive silica containing glass further comprises calcium and phosphate ions, or said preparation further consists essentially of calcium and phosphate providing sources.

4. The method of claim 1, wherein said preparation has a pH equal to or greater than 9.5.

5. The method of claim 1, wherein said crystallization of apatite in dental tubules and/or on the tooth surface occurs within about one week.

6. A pharmaceutical preparation suitable for reducing pulpal irritation and/or strengthening the structure of a tooth, consisting essentially of a glass phase containing bioactive silica containing glass, wherein
said preparation is sufficiently moist to maintain chemical interactions between the glass phase and dentine so as to permit transfer of silica into dentine, and
said bioactive silica containing glass is present in an amount which renders said preparation capable of rapid release of silica in a concentration effective to induce crystallization of apatite in dental tubules and/or on the tooth surface.

7. The preparation of claim 6, wherein said preparation has a pH equal to or greater than 9.5.

8. The preparation according to claim 6, further consisting essentially of calcium and phosphate sources.

9. The preparation according to claim 6, wherein said preparation further consists essentially of an agent for promoting the growth of crystals in the dentine tissue.

10. The preparation according to claim 6, wherein the glass phase is solely Si-oxide or Si-hydroxide, or comprises in addition to Si-oxide or Si-hydroxide, at least one member of the group consisting of Na, K, Ca, Mg, B, Ti, Al, P, N and F, or is a solution comprising Si—OH groups.

11. The preparation of claim 10, wherein the composition of the glass phase is as follows:

| | |
|---|---|
| $SiO_2$ or Si-gel | 1–100% |
| CaO | 0–40% |
| $P_2O_5$ | 0–60% |
| $Na_2O$ | 0–45% |
| $K_2O$ | 0–45% |
| MgO | 0–40%. |

12. The preparation of claim 10, wherein the composition of the glass phase is as follows: $SiO_2$ 53%; CaO 20%; $P_2O_5$ 4% and $Na_2O$ 23%.

13. The preparation of claim 10, wherein the composition of the glass phase is as follows: $SiO_2$ 45%; CaO 22%; $P_2O_5$ 7%; $Na_2O$ 24% and $B_2O_3$ 2%.

14. The preparation of claim 6, wherein the preparation further consists essentially of ceramic powder.

15. The preparation according to claim 1, wherein said physiologically suitable binder is fibrinogen or chitin.

16. The preparation according to claim 8, wherein the glass phase is solely Si-oxide or Si-hydroxide, or comprises in addition to Si-oxide or Si-hydroxide at least one member of the group consisting of Na, K, Ca, Mg, B, Ti, Al, P, N and F, or is a solution comprising Si—OH groups.

17. The preparation according to claim 9, wherein the glass phase is solely Si-oxide or Si-hydroxide, or comprises in addition to Si-oxide or Si-hydroxide, at least one member of the group consisting of Na, K, Ca, Mg, B, Ti, Al, P, N and F, or is a solution comprising Si—OH groups.

18. The preparation according to claim 10, wherein said glass phase is silica gel.

19. The preparation according to claim 16, wherein said glass phase is silica gel.

20. The preparation according to claim 17, wherein said glass phase is silica gel.

* * * * *